United States Patent [19]
Simmons et al.

[11] Patent Number: 5,752,511
[45] Date of Patent: May 19, 1998

[54] UNIVERSAL MEDICAL TUBE RETAINER AND NASAL WALL TISSUE DILATOR

[76] Inventors: Carl J. Simmons, P.O. Box 668, Nolensville, Tenn. 37135; Robert N. Sadler, 3713 Sycamore Ln., Nashville, Tenn. 37215

[21] Appl. No.: 755,404

[22] Filed: Nov. 22, 1996

[51] Int. Cl.$^6$ .................................................. A61M 15/08
[52] U.S. Cl. ........................ 128/207.18; 128/206.11; 128/206.14; 128/DIG. 26
[58] Field of Search .................... 128/206.11, 206.14, 128/206.18, 207.18, DIG. 26; 604/177, 180

[56] References Cited

U.S. PATENT DOCUMENTS

| | | | |
|---|---|---|---|
| 3,046,989 | 7/1962 | Hill | 604/180 |
| 4,120,304 | 10/1978 | Moor | 604/180 |
| 4,122,857 | 10/1978 | Haerr | 604/180 |
| 4,736,741 | 4/1988 | Payton et al. | 128/207.18 |
| 4,804,374 | 2/1989 | Laskody | 604/180 |
| 4,823,789 | 4/1989 | Beisang, III | 128/207.18 |
| 4,932,943 | 6/1990 | Nowak | 604/180 |
| 4,986,815 | 1/1991 | Schneider | 604/180 |
| 5,097,827 | 3/1992 | Izumi | 128/207.18 |
| 5,117,818 | 6/1992 | Palfy | 128/DIG. 26 |
| 5,156,641 | 10/1992 | White | 128/207.18 |
| 5,172,688 | 12/1992 | Dillon | 128/207.18 |
| 5,185,005 | 2/1993 | Ballantyne | 604/174 |
| 5,476,091 | 12/1995 | Johnson | 128/200.24 |
| 5,513,635 | 5/1996 | Bedi | 128/DIG. 26 |
| 5,535,739 | 7/1996 | Rapoport et al. | 128/207.18 |

*Primary Examiner*—Aaron J. Lewis
*Attorney, Agent, or Firm*—Elman & Associates

[57] ABSTRACT

A method for expanding the volume of interior nasal air passages (65 and 67) by introducing separating forces in anatomical outer nasal wall tissues (62 and 64) to enhance oxygen flow and minimize obstruction caused by the presence of nasally inserted medical tubing, which further supports and retains various combinations of oxygen cannula (68), a nasogastric suction tube (35), or an enteral feeding tube (40). This method includes a device containing a clip assembly (14), adjustable arm (18) and dilator patch assembly (12). The primary purposes of this method are to reduce incidence of secondary infection, increase efficacy of oxygen therapy and improve patient comfort.

16 Claims, 6 Drawing Sheets

UNIVERSAL MEDICAL TUBE RETAINER AND NASAL WALL TISSUE DILATOR

CROSS REFERENCES TO RELATED PATENTS

The invention contains an element of like structural composition to that of U.S. Pat. No. 5,476,091, a Dilator For Anatomical Outer Wall Tissues Which Is Adhesively Mounted, issued to B. Johnson, 12/19/95, and adhesively mounted nasal dilator strips of similar construction.

FIELD OF INVENTION

This invention relates to the field of medical devices, specifically to an improved method of retaining medical tubing combined with expansion of internal nasal passage volume by dilation of outer wall tissues.

BACKGROUND OF THE INVENTION

Oxygen and other therapies requiring the insertion of medical tubing through the nasal cavity have experienced several problems. First, it is difficult and uncomfortable to combine therapies requiring nasal tubing. Oxygen treatment in the presence of a nasogastric tube is one example. In such a case critical oxygen delivery can easily be interfered with by the presence of the nasogastric tube. Both nasal opening interference caused by competing tubing or injury, and limited internal nasal passage volume can limit therapy effectiveness.

In addition, without any means to hold the tubing stable it is easy for normal patient movement to disturb or dislodge such tubing. Nasogastric and feeding tubes are commonly held in place by the subjective placement of adhesive medical tape strips to one side of the patient's face. As such, effectiveness of application is left to the skill of the medical attendant, and can interfere with patient comfort and contradict the presence of oxygen cannula.

Prolonged friction of nasally inserted tubing with interior nasal tissues is another common problem which can lead to secondary infections caused by unsupported or inadequately supported tubing. As such, the presence of more than one type of tubing within a nasal passage substantially increases the chance of tissue infection without remedial and integrated physical support.

Several prior patents meant to secure nasogastric medical tubing to patients (U.S. Pat. Nos. 5,185,005, to Ballantyne, 2/9/93 : 4,932,943 to Nowak, 6/12/90 : 4,986,815 to Schneider, 1/22/91 : 5,172,688 to Dillon, 12/22/92 : 5,156,641 to White, 10/20/92 : 4,823,789 to Beisang, 4/25/89), do not address these problems satisfactorily. One limitation is that none are intended to reduce incidence of secondary infection when therapies requiring nasal tubing in combination are present.

Also, all prior art discovered, including the previous patents and U.S. Pat. No. 5,476,091 to B. Johnson, 12/19/95, fails to combine nasal passage dilator technology with a medical tubing retainer so as to increase air passage volume in the presence of medical tubing, facilitate insertion of such tubing, or increase the efficiency of oxygen therapy when in use.

It is also notable that none of the prior art provides an effective means for retaining commonly used oxygen cannula in a stable and integrated fashion in conjunction with the presence of either a nasogastric or feeding tube.

On a specific basis, there are several other ways in which the prior art fails to address prevention of secondary infection and patient comfort in cases where combined therapies are required. U.S. Pat. No. 5,156,641 to White, 10/20/92, requires the use of a non-standard nasogastric tube to accommodate a delicate connector system intended to secure a nose patch to the tube. Standard medical tubing would not be compatible with this system. Also, the adjustment link described in this system would have little capability for bearing subtle pull and twist stresses. These stresses are commonly present and result in friction between tubing and internal nasal tissues which often produces tissue trauma and secondary infection.

U.S. Pat. No. 5,185,005 to Ballantyne, 2/9/93, is a substantially invasive system requiring a high level of attendant skill for proper insertion. In addition this invention does little to reduce friction with nasal tissues and may significantly increase risk of secondary infection if not properly inserted. Further, the device appears to effectively prevent other treatments requiring nasally inserted tubing or oxygen by occupying the nasal passages with hardware for the apparatus and placing an anchoring clip across the breadth of the nasal passages when in use.

Specific limitations are also present with U.S. Pat. No. 5,172,688 to Dillon, 12/22/92, in that the system allows for insertion of nasogastric tubing into only one specific nostril. Injury or disease to nasal passages preventing the tubing holder from being aligned with the open nostril would render this device of little practical use. As depicted in the art this device would also appear to present significant potential for increased friction between the nasogastric tube and outer wall tissues of the corresponding nasal passage.

U.S. Pat. No. 4,823,789 to Beisang, 4/25/89, fully consists of flexible adhesively mounted elements which offer little supportive structure and effectively replicate the current methods of taping nasally mounted tubing to the face with strips of medical tape. As with application of tape strips, this device would do little to reduce friction with adjoining tissues and, although restricting tubing from being pulled out, lacks the physical support necessary for limiting the tubing's tendency to twist and push against nasal passages.

U.S. Pat. Nos. 4,932,943 to Nowak, 6/12/90, and 4,986,815 to Schneider, 1/22/91, are very much alike in practice. Besides limitations already mentioned common to all the prior art, these two devices have the further disadvantage of orienting a nasogastric tube directly in line with and above the center point of the nostril area. Since the center point of each nostril is off this center point the tubing is pushed into an orientation where pressure on interior nasal tissues and misalignment of the tubing with the nasal passage used will likely result. Also, an actual production sample of these inventions shows that the clamping jaws for holding tubing is both difficult to manipulate and cannot be easily released by medical personnel when desirous to do so. It is further noted that the location of the clamping jaws can interfere with the presence of standard oxygen cannula.

OBJECTS AND ADVANTAGES

Accordingly several objects and advantages of our method are inclusive of a device for combining already existing adhesively mounted nasal dilator technology with a multiple purpose medical tubing retainer. These include the ability to retain any clinically valid combination of oxygen, feeding or nasogastric medical tubing, reduce incidence of secondary infection by preventing friction with adjoining tissues, expand internal nasal passage volume to facilitate the insertion and presence of medical tubing, and improve the efficiency of oxygen delivery therapy through increased nasal cavity volume.

Other objects and advantages of the invention are that more aggressive adhesives may be employed than those used on adhesively mounted nasal dilators found at retail outlets, and that the device permits adjustment of the retainer to accommodate different nose sizes, shapes and physiological condition.

Further objects and advantages of our invention will become apparent from a consideration of the drawings and ensuing description.

REFERENCE NUMERALS IN DRAWINGS

| 12    | dilator patch assembly       |
|-------|------------------------------|
| 14    | retainer clip assembly       |
| 15    | retainer clip                |
| 16    | nose bridge                  |
| 18    | adjustable arm               |
| 19    | adjustable arm               |
| 20a&b | feeding tube fixture         |
| 22    | oxygen cannula detent        |
| 24    | upper cannula retainer       |
| 26    | facial contour detent        |
| 28a&b | lower cannula retainers      |
| 30    | top material strip           |
| 32    | molded nosepiece             |
| 34    | typical nasal dilator strip  |
| 35    | nasogastric tube             |
| 36    | n.g./ox. clip corners        |
| 38    | oxygen tube                  |
| 39    | adjustable arm serrations    |
| 40    | feeding tube                 |
| 42    | standard oxygen supply tube  |
| 44    | custom oxygen supply fixture |

-continued

| 46a&b | nasogastric/oxygen tube retainer clip |
|-------|---------------------------------------|
| 48a&b | resilient bands                       |
| 50    | right adhesive release backing        |
| 51    | left adhesive release backing         |
| 54a&b | interface adhesive material           |
| 56    | medical grade adhesive                |
| 58    | tip of nose                           |
| 60    | nose structure                        |
| 62    | right nasal tissue                    |
| 64    | left nasal tissue                     |
| 65    | right nasal passage                   |
| 67    | left nasal passage                    |
| 68    | oxygen cannula assembly               |

SUMMARY

The invention provides a method for expanding interior nasal cavity volume by introducing separating forces in anatomical outer wall tissues to enhance oxygen flow and minimize obstruction caused by the presence of medical tubing. The method further retains any typical combination of medical tubing, including oxygen cannula, commonly administered through the nasal cavity. This method of application also enlarges volume of interior nasal passages to facilitate tubing insertion, and limits contact and friction of the interior anatomical tissues with tubing to reduce incidence of secondary tissue infection.

DESCRIPTION OF THE PREFERRED EMBODIMENTS (FIGS. 1–7B)

Figure 1:
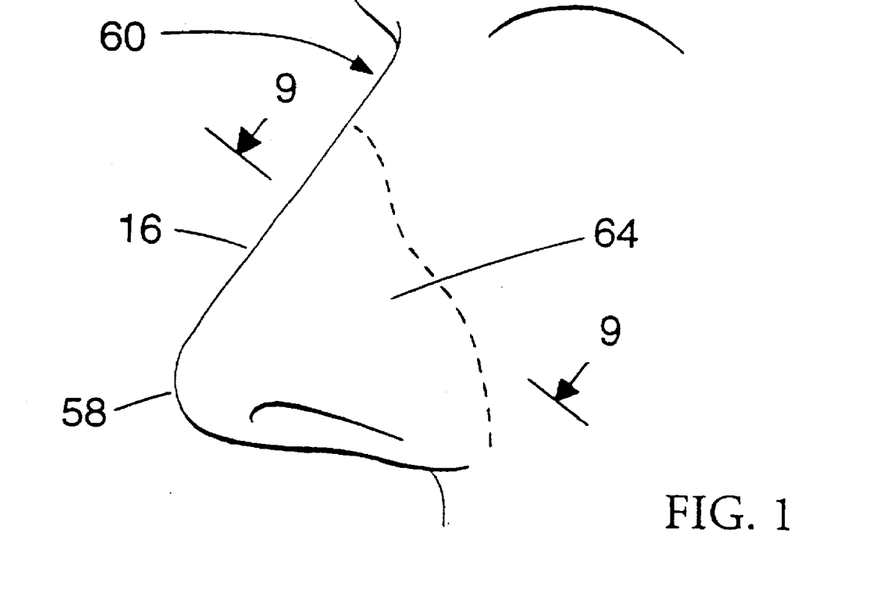
FIG. 1 is a view drawing of the human nose for reference to FIG. 2 and FIG. 8A through FIG. 9B.
Figure 2:
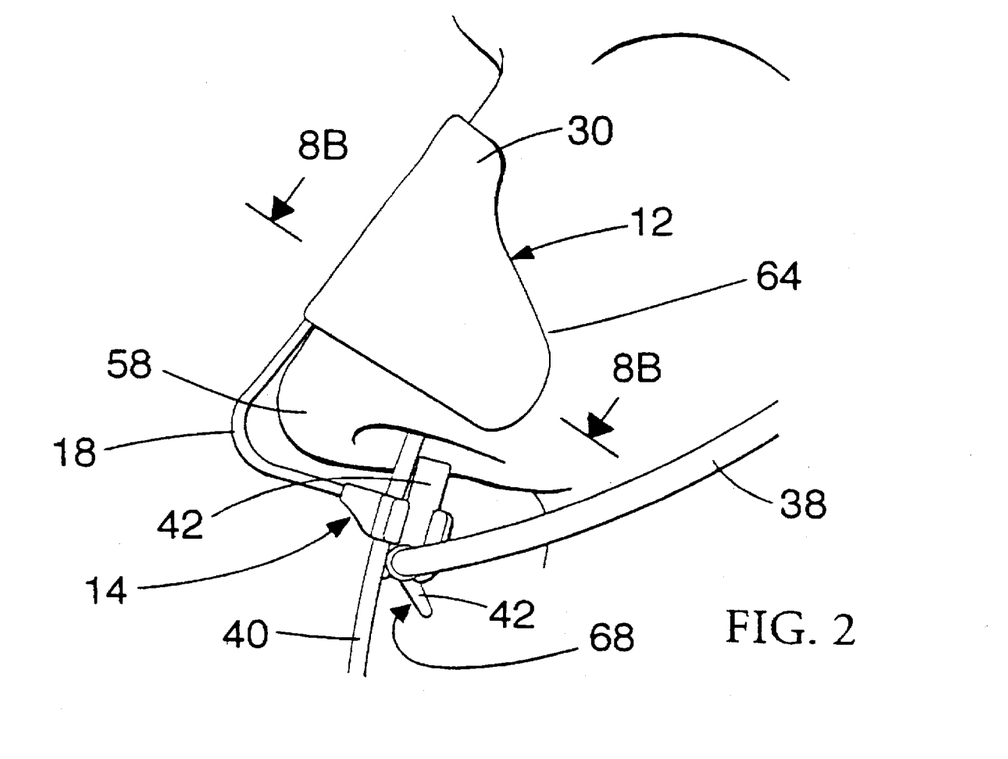
FIG. 2 is a elevation drawing of the preferred embodiment mounted to a human nose with a feeding tube and oxygen cannula in use.
Figures 3, 4:
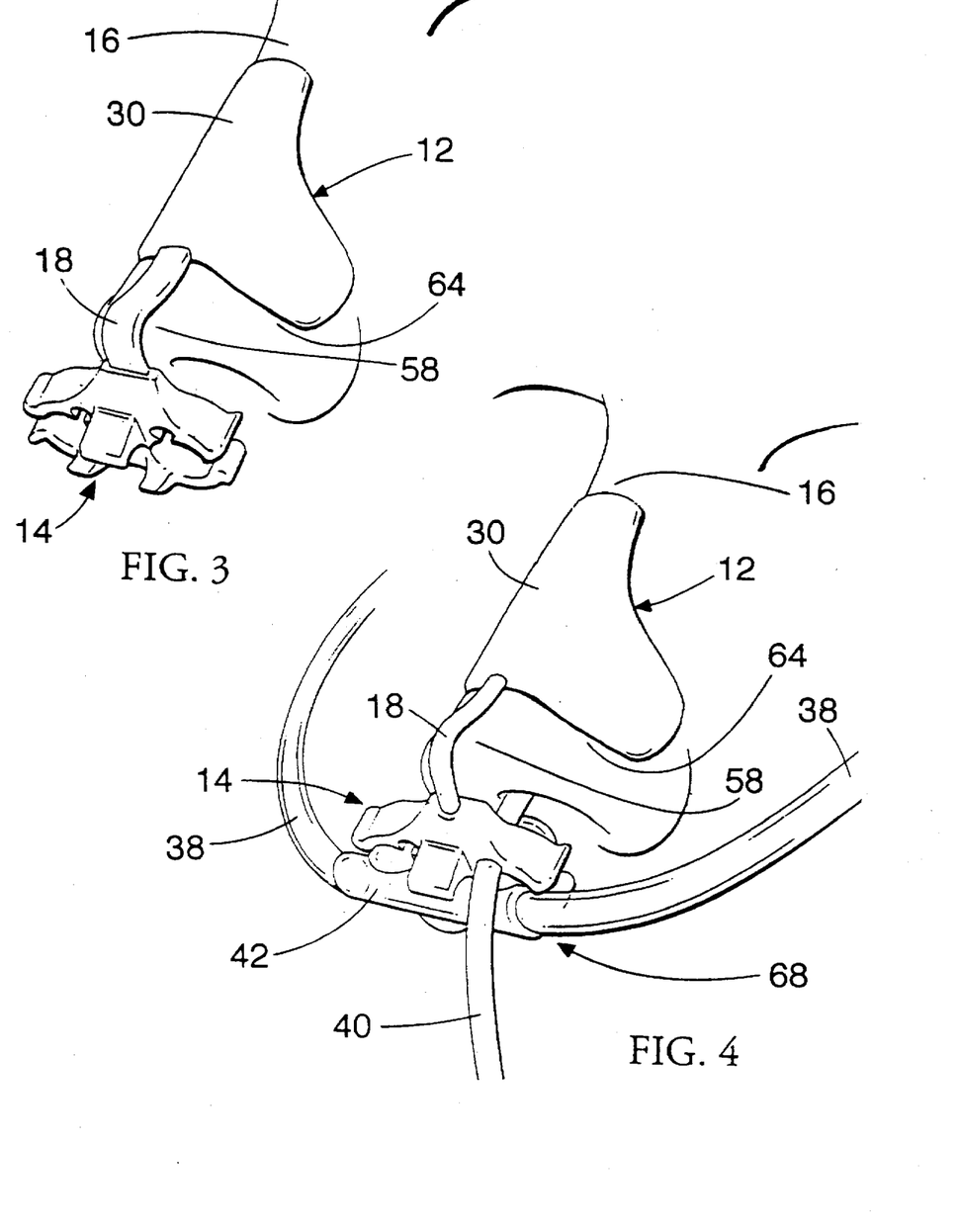
FIG. 3 is a perspective drawing of the preferred embodiment without the presence of medical tubing.
FIG. 4 is a perspective drawing of an alternate embodiment with oxygen cannula and a feeding tube attached.

FIG. 2 depicts a pictorial view of the preferred embodiment with oxygen tubing 38, standard oxygen supply tube 42, and feeding tube 40 attached to retainer clip assembly 14. Oxygen tubing 38 and oxygen supply tube 42 comprise what is commonly referred to as oxygen cannula 68 to those skilled in the art of medical fixtures. FIG. 3 shows the identical embodiment to that in FIG. 2, but without tubing attached, while FIG. 4 is an alternative embodiment with regard to the type of adjustable arm 19 used.

In basic construction retainer clip 15 is to be formed of a semi-rigid, injection molded thermoplastic such as high density polyethylene or acetal. Such a material or an equivalent is desirable since structural integrity to provide support for tubing, flexibility to provide gripping tension upon the nasogastric tubing 35 shown in FIG. 5 and FIG. 6, and a clinically inert material are all requirements for effective performance. Retainer clip 15 must not consist of a brittle material, as it would be highly undesirable to have small pieces break off during use.

Figures 7A, 7B:
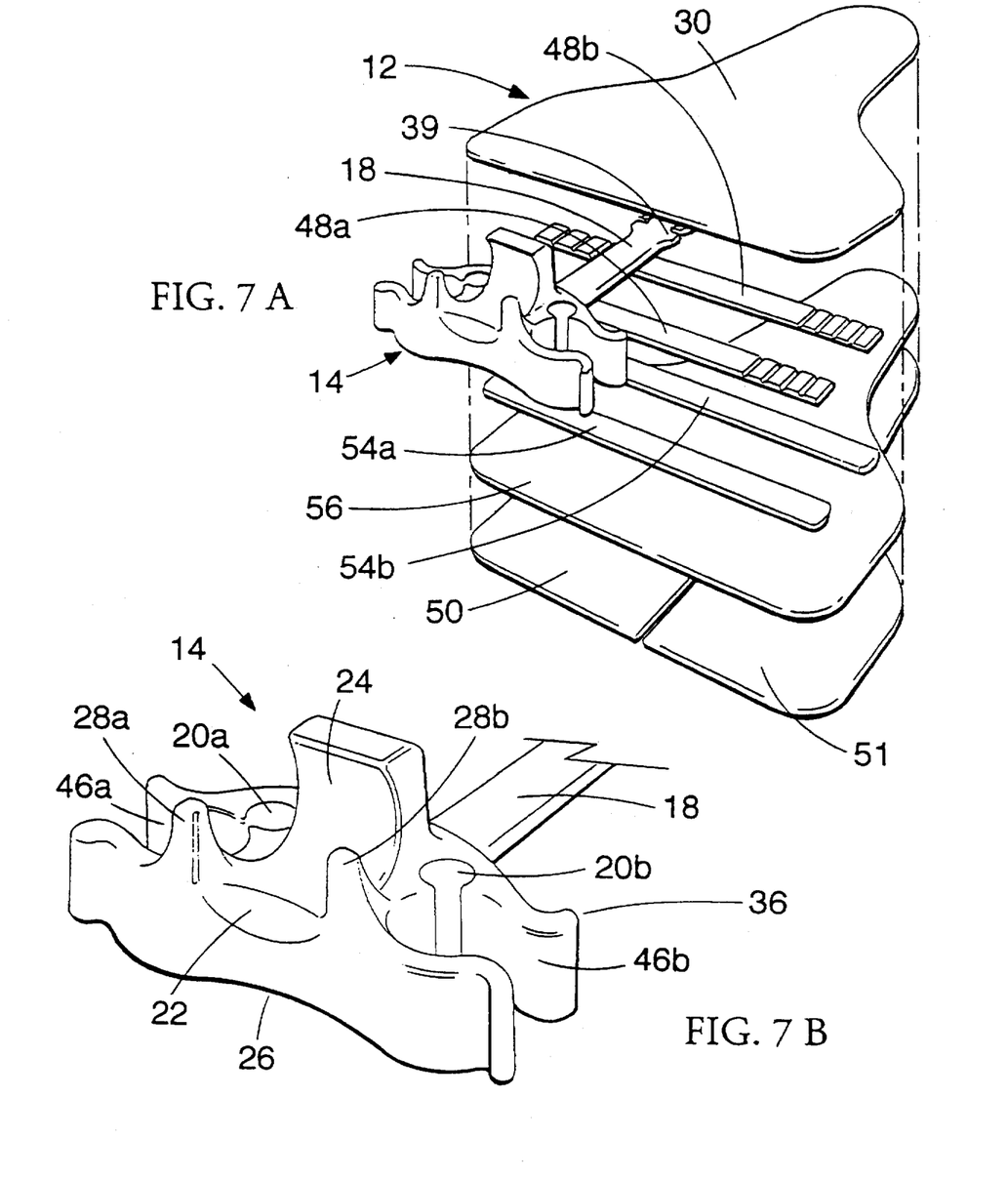
FIG. 7A is an exploded drawing of the preferred embodiment using typical nasal dilator strip technology.
FIG. 7B is a detail drawing of the tubing retainer of the preferred embodiment.

The various features of retainer clip 15 are illustrated in detail in FIG. 7B. Oxygen supply tube 42 or custom oxygen supply fixture 44 are effectively retained by a combination of upper cannula retainer 24 and lower cannula retainers 28a and 28b. These elements provide a resultant interior diameter of 5 mm and extend slightly over center as shown in upper cannula retainer 24 and lower cannula retainers 28a and 28b to capture oxygen supply tube 42 or custom oxygen supply fixture 44. In order to fit to a standard oxygen supply tube 42 commonly used in an oxygen cannula assembly 68, the distance from center to center of interior openings to hold tubing in each nasogastric/oxygen supply clip 46a and 46b should be 15 mm. Depending on the flexibility of material used to form retainer clip 15 the interior openings for nasogastric/oxygen clips 46a and 46b should each be approximately 5 mm in diameter and be expandable to 6 mm diameter without compressing standard 16 or 18 french size nasogastric tubing so as to adversely affect specified suction rates. The attendant openings to allow tube entry to nasogastric/oxygen tube clips 46a and 46b will likewise vary slightly according to exact material used in clip assembly 14, but worked well at 4 mm in inventor prototypes. By incorporating a symmetrical shape to retainer clip 15 it performs the dual functions of accommodating a standard oxygen supply tube 42 from an oxygen cannula assembly 68, and also makes insertion of a nasogastric tube 35 feasible in either nostril opening.

Nasogastric/oxygen clip corners 36 as shown at the tube entry flanges which assist clipping of oversize tubing should contain generously rounded edges on all surfaces to eliminate irritation to surrounding skin. In addition, it is recommended to incorporate a facial contour detent 26 into retainer clip 15 to reduce incidence of contact with the fleshy formation found between the base of the nose and the upper lip, also known as the Filtrum. On the plane of facial contour detent 26 an added oxygen cannula detent 22 eliminates interference with many standard oxygen supply tubes 42 which incorporate a semi-circular tab opposite and between the two oxygen outlets. This tab is shown in profile in FIG. 2.

In order to fit a standard 8 french enteral feeding tube for insertion in either nostril, retainer clip 15 also incorporates feeding tube fixtures 20a and 20b symmetrically and in the orientation indicated in FIG. 7B. Inventor prototypes indicate that feeding tube fixtures 20a and 20b be 3 mm in diameter, with attendant openings to allow tube entry of approximately 1.5 mm. It is important that feeding tube fixtures 20a and 20b be oriented in a fashion that when an 18 french nasogastric tube 35 or standard oxygen supply fixture 42 is in use in either nasogastric/oxygen tube clip 46a or 46b, a feeding tube 40 in either feeding tube fixture 20a or 20b would not interfere with its operation.

Figures 5, 6:
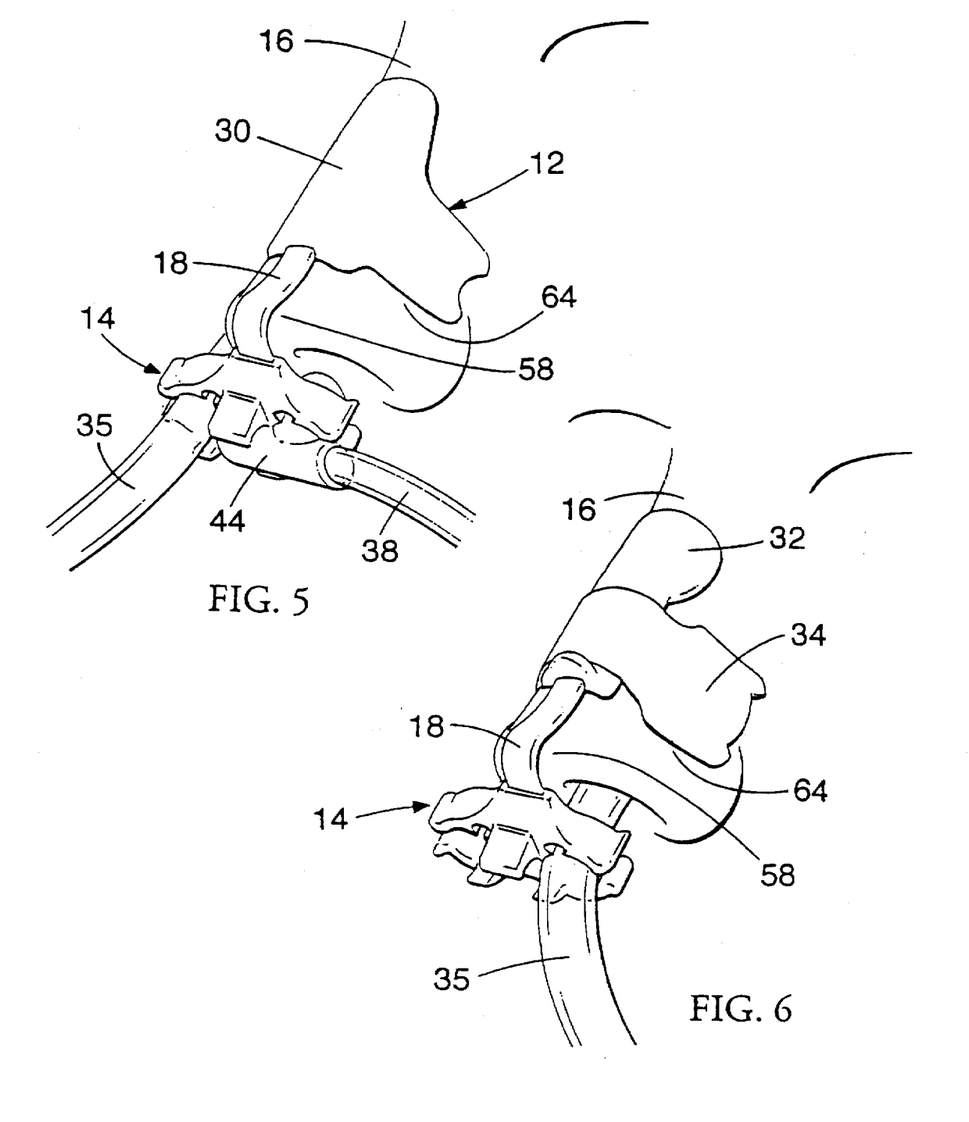
FIG. 5 is a perspective drawing of an alternate embodiment with a nasogastric tube and custom oxygen cannula attached.
FIG. 6 is a perspective drawing of an alternate embodiment with a nasogastric tube attached, and secured to the nose bridge with a standard adhesively mounted nasal dilator strip.

In the preferred and alternate embodiments adjustable arm 18 would be insert molded with retainer clip 15 to assure a durable one-piece retainer clip assembly 14 with no opportunity for separation as shown FIG. 6. As shown in FIG. 3 and FIG. 4, adjustable arm 18 or 19 could be of different materials providing a material is used that can be bent by finger pressure and will remain in place after such adjustment. Adjustable arm 18 or 19 has been reduced to practice in acceptable prototypes by using either 14 gage, solid core copper, coated wire, as indicated in FIG. 4, or flat metal stock as shown in FIG. 3 and FIG. 5 consisting of 0.5 mm thick, corrosion resistant copper beryllium or an equivalent. For adjustment to most adult noses preliminary prototypes indicate an exposed length of 17 mm is advisable for adjustable arm 18 between retainer clip 15 and dilator patch assembly 12.

Figure 8:
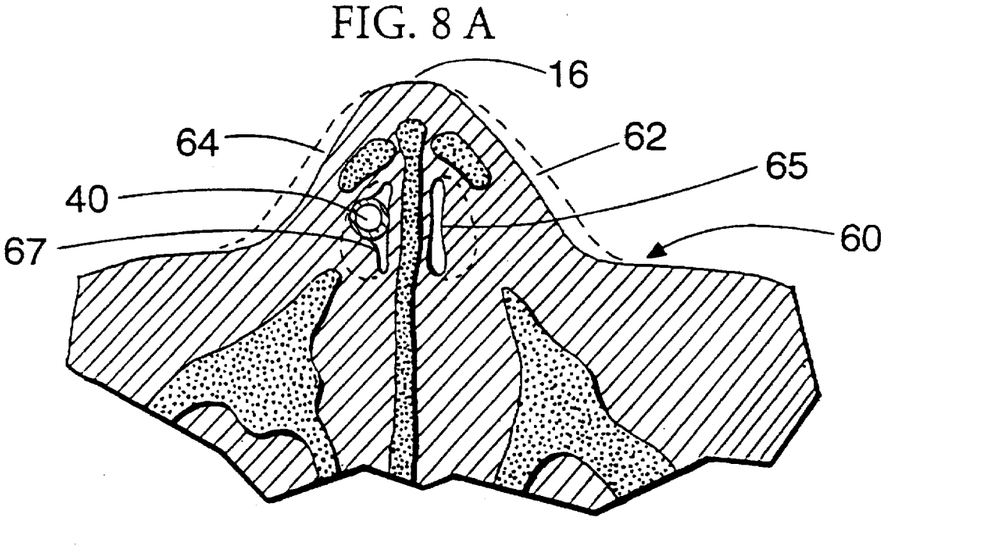
FIG. 8A is a sectional view taken from FIG. 4 of a nasal cavity with a standard enteral feeding tube present with little air flow through the nasal passage.
FIG. 8B is a sectional view taken from FIG. 2 of a nasal cavity assisted by nasal dilator technology with an appreciable air flow in the nasal passage, and with a standard enteral feeding tube present.

FIGS. 4, 5, and 6 show retainer clip assembly 14 holding a variety of tubing combinations including standard oxygen supply tubing 42 and a feeding tube 40, nasogastric tube 35 and a custom oxygen supply fixture 44, and a nasogastric tube 35 alone. There is no clinical need for accommodating a feeding tube 40 and nasogastric tube 35 at the same time. FIG. 4 and FIG. 5 indicate two alternate embodiments of shapes which dilator patch assembly 12 could take. The essential factor is that the patch extend externally over the nasal wall tissue areas which would benefit from dilation. These areas are depicted as nasal tissue right 62 and nasal tissue left 64 in FIG. 8B.

The construction of dilator patch assembly 12 is generally indicated in FIG. 7A and is similar to existing nasal dilator strip technology. A more detailed example of this technology can be found in U.S. Pat. No. 5,476,091 to B. Johnson, 12/19/95, titled Dilator For Anatomical Outer Wall Tissues Which Is Adhesively Mounted. Adjustable arm 18 is therefore contained within dilator patch assembly 12 by means of lamination technology utilizing heat seal, pressure adhesive or a similar manufacturing process, and extends throughout the length of dilator patch assembly 12. To provide maximum ability for the dilator patch assembly 12 to retain adjustable arm 18, a series of adjustable arm serrations 39 may be provided to secure it within the lamination.

Indicated are resilient bands 48a and 48b which provide an effective spring constant to provide the desired pull on the outer wall tissues of the user's nose, the exact performance of which are adjustable by material, thickness, length, width and geometry of notches. Resilient bands 48a and 48b are secured by flexible strips of interface adhesive material 54a and 54b to the top side of base material consisting of medical grade adhesive 56. An example of a suitable compound for interface adhesive material 54a and 54b would be an acrylic, pressure sensitive, bio-compatible transfer tape such as 3M 1509 available from Minnesota Mining & Manufacturing Company, Inc. Right adhesive release backing 50 and left adhesive release backing 51 cover medical grade adhesive 56 before use, and are readily removeable from medical grade adhesive 56 prior to application on a patient's nose. The outer contour of dilator patch assembly 12 is variable to the extent that it conforms to performance requirements stated herein, and is manufacturable by die cutting processes common to similar adhesive medical patches and strips.

FIG. 6 depicts another alternate embodiment of the Universal Retainer/Nasal Dilator consisting of a molded nosepiece 32 attached to nose bridge 16 by means of a typical nasal dilator strip 34 which is adhesively mounted. Research conducted by the inventors indicates that an FDA approved thermoplastic rubber like Dynaflex G6713 would be a suitable material for molded nosepiece 32 as it conforms to nose bridge 16 contours, "grips" the skin by becoming slightly tacky when warm, and is FDA approved for medical applications. This material would permit the entire device to be insert injection molded in a one step process. The inventors also considered using the same material and assembly in this embodiment as skin barrier used for ostomy patients, an example of which is Hollister Inc. Premium Skin Barrier #7800, to perform the function of molded nosepiece 32. A primary feature of this material is that it forms a strong adhesive quality to skin when warm and conforms easily. Both materials and methods of construction for molded nosepiece 32 would retain the advantages of accommodating nasally inserted medical tubing in combination with oxygen therapy, and would utilize the dilation forces of nasal dilator strip 34 to expand interior nasal passage volume to assist such therapies and increase patient comfort.

OPERATION (FIGS. 8A–9B)

FIG. 8A through FIG. 9B depict anatomical factors pertaining to the performance of the claimed invention. These figures show a nose structure 60 including tissue generally referred to as nose bridge 16, right nasal passage 65, left nasal passage 67, right nasal tissue 62, and left nasal tissue 64.

Figure 9A:
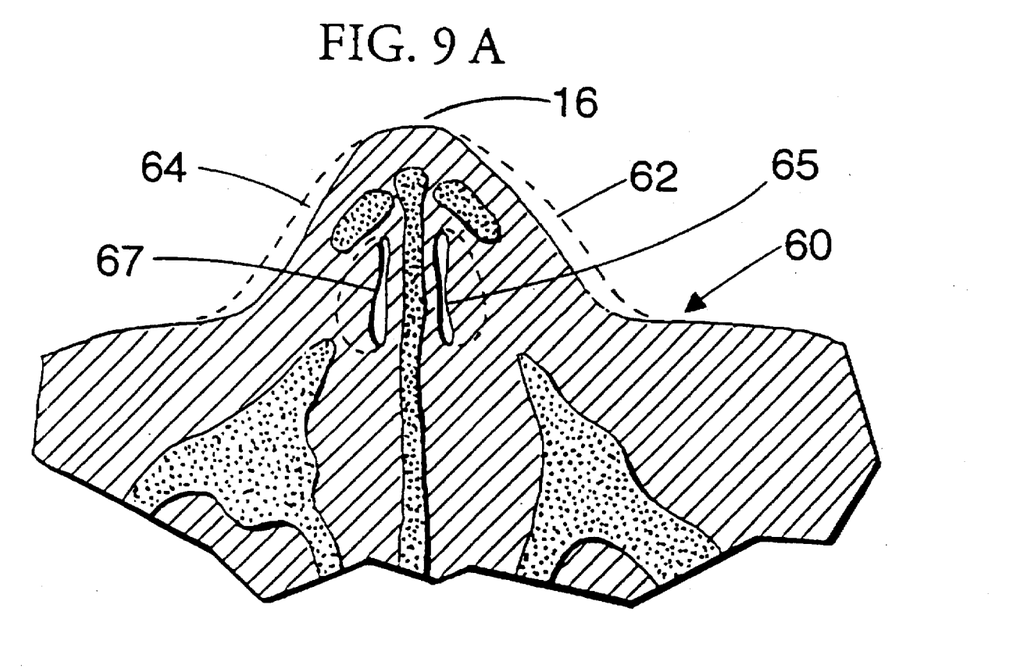
FIG. 9A is a sectional view taken from FIG. 1 of a nasal cavity through which little flow of air is passing.
Figure 9B:
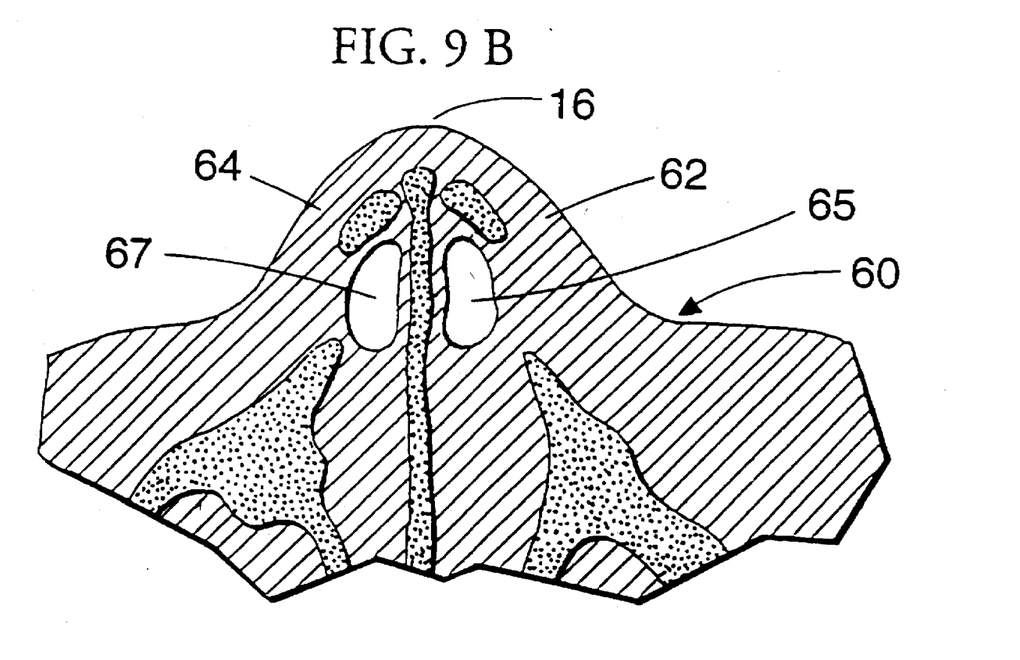
FIG. 9B is a sectional view of a nasal cavity with an appreciable air flow through the nasal passage.

In FIG. 9B, nose structure 60 is again shown in a sectional view. The state of nasal passages 65 and 67 is that occurring in the portion of the breathing cycle when little air is flowing through them, and are thus the air passages of a person that is healthy and without injury to nasal tissues.

The process of inhaling air causes nasal tissues 62 and 64 to draw inward slightly as suction forces are caused within air passages 65 and 67. Conversely, in the presence of inflammation or obstruction to air passages 65 and 67 caused by illness, allergy or injury, inhalation can often result in dramatically higher suction forces as the person attempts to inhale sufficient air. Nasal tissues 62 and 64 can then pull inward significantly, in severe cases to the point of near closure of air passages 65 and 67. This condition is indicated in FIG. 9A, and is most severe at the juncture of the nasal passage bone and skull where indicated along the dotted line in FIG. 1. This area is known as the nasal valve, and the severity of closure is determined by the size of this valve in each person.

Hospital patients requiring oxygen, nasogastric suction or enteral feeding commonly suffer from the type of nasal inflammation described, a condition further exacerbated by the presence of medical tubing. Such a condition is illustrated in FIG. 8A, a sectional view of nose structure 60 with no separation of nasal tissues 62 and 64 as would be caused by nasal dilator patch assembly 12.

Even patients with normally clear and open air passages can experience problems with nasal inflammation when medical tubing is in friction with surrounding tissues, and in any case efficacy of oxygen therapy is improved the more nasal tissues 62 and 64 are held open. Therefore, FIG. 8B depicts the benefits of adding nasal dilator technology to the practice of nasally applied medical therapies, as described in the previous scenarios. This condition is a clear improvement over previous medical tubing retainers which fail to address retention of oxygen cannula or enteral feeding tubes, and do not utilize nasal dilator technology.

Existing nasal dilator technology of the type inclusive of the Universal Retainer/Nasal Dilator is a remedy to these nasal blockage problems. Therefore, when used in conjunction with an adjustable, articulated universal tubing retainer the claimed invention is a new and medically effective method for retaining a combination of tubing fixtures for nasally delivered therapies, reducing incidence of secondary infection, enhancing efficacy of oxygen therapy by expanding nasal air passages, and increasing patient comfort.

CONCLUSIONS, RAMIFICATIONS AND SCOPE OF INVENTION

Thus the reader will see that the Universal Medical Tube Retainer & Nasal Wall Tissue Dilator provides a highly effective and economical method for increasing efficacy and patient comfort for therapies requiring oxygen, gastric suction or enteral feeding which can be used by properly trained medical attendants of average skill.

While the above description contains many specifics of the claimed invention these should not be construed as limitations on the scope of the method, but rather as manifestations of both a preferred and small number of alternate embodiments thereof. For example clip assembly 14 could exclude upper cannula retainer 24 and lower cannula retainers 28a and 28b and still contain provision to retain either a nasogastric or feeding tube to reduce incidence of secondary infection while providing the therapeutic advantages of nasal dilation with such tubing. As another example, several alterations could be made in the exact construction of dilator patch assembly 12 without altering the intention of the patch to be an adhesively applied nasal dilator to assist in the function of supporting and directing a combination of therapies with relation to increased nasal passage volume.

Therefore, although the Universal Medical Tube Retainer and Nasal Wall Tissue Dilator has been described with reference to the preferred and several alternate embodiments, workers skilled in the art will recognize that changes may be made in form and detail without departing from the spirit and scope of the invention.

Accordingly, the scope of the invention should be determined not by the specific embodiments illustrated, but by the appended claims and their legal equivalents.

What is claimed is:

1. A medical device for facilitating nasal insertion of medical tubing and for improving the flow of oxygen through a patient's nasal passages comprising:

(a) a nasal dilator including a resilient band and a patch having adhesive thereon for application to a patient's nose, said nasal dilator having means for introducing separating forces in outer nasal wall tissues, thereby expanding the volume of interior nasal passages; and (b) a retainer clip assembly, said retainer clip assembly extending distally of a patient's nose from said nasal dilator and having means for supporting and retaining medical tubing near the entrance to a patient's nose.

2. The medical device of claim 1 wherein said retainer clip assembly is adapted for supporting and retaining a plurality of medical tubes.

3. The medical device of claim 2 wherein said retainer clip assembly is adapted for supporting and retaining a plurality of medical tubes of a plurality of sizes.

4. The medical device of claim 3, wherein said retainer clip assembly is adapted for supporting medical tubes of the sizes of oxygen cannula, nasogastric tubing and enteral tubing.

5. The medical device of claim 1 wherein said nasal dilator further comprises:
    an interface strip.

6. The medical device of claim 1 wherein said retainer clip assembly comprises:
    a retainer clip adapted for removably retaining a plurality of nasally inserted medical tubes and an arm extending from said nasal dilator to said retainer clip.

7. The medical device of claim 6 wherein said retainer clip is of a resilient material and partially encloses a plurality of generally cylindrical channels, each channel being adapted to support and retain medical tubing of a predetermined standard diameter.

8. The medical device of claim 6 wherein said arm is of a material which remains in place after bending by finger pressure, whereby said arm is adjustable to position said clip at a nasal opening.

9. A method of using the medical device of claim 8 for inserting and supporting medical tubing in a patient's nose, comprising:

(a) providing a medical device in accordance with claim 8;

(b) fitting it to a patient's nasal anatomy by bending the adjustable arm to position the retainer clip so that it will be under and adjacent to the patient's nose when the device is adhered to the patient's outer nasal tissue;

(c) adhering the nasal dilator to the patient's outer nasal tissue, thereby providing an outward separating force to the nasal anatomy, enlarging the interior nasal passage; and (d) placing medical tubing in said retainer clip, so as to be supported and retained thereby.

10. The medical device of claim 8 wherein said arm comprises a coated bendable metal wire or strip.

11. The medical device of claim 10 wherein said retainer clip is formed with a pair of cylindrical channels of differing diameters, together having an &-shaped cross section.

12. The medical device of claim 11 wherein said retainer clip is symmetrically formed with two pairs of cylindrical channels of differing diameters, the axes of each pair of channels being spaced apart from each other approximately the distance between the axes of a typical patient's nostrils.

13. The medical device of claim 12 wherein said retainer clip further includes a pair of cannula retainers and an oxygen cannula detent, and in which the inner diameter of the smaller channels is sized for supporting an enteral feeding tube and the inner diameter of the larger channels is sized for supporting a nasogastric tube or oxygen cannula, whereby oxygen cannula supplying both nostrils and an enteral feeding tube may simultaneously be supported by said retainer clip, and alternatively an oxygen supply fixture supplying one nostril and a nasogastric tube extending through the other nostril may simultaneously be supported by said retainer clip.

14. A medical device comprising a stack of the following elements laminated together:
   (i) an adhesive release strip;
   (ii) a patch having medical grade adhesive on the side adapted to face a patient's nose;
   (iii) a pair of parallel interface adhesive strips having adhesive material on both sides;
   (iv) a pair of resilient bands having a spring constant for producing a pulling force on a patient's outer nasal tissues;
   (v) a retainer clip assembly extending distally of a patient's nose from said patch and having means for supporting and retaining medical tubing near the entrance to a patient's nose, and
   (vi) a top material strip.

15. The medical device of claim 14, wherein said retainer clip assembly (v) comprises:
   an adjustable arm laminated between said resilient bands and said top material strip, and
   a retainer clip for said medical tubing at the end of said adjustable arm.

16. A method for facilitating nasal insertion of medical tubing and for improving the flow of oxygen through a patient's nasal passages, comprising the steps of:
   (a) providing a nasal dilator including a resilient band and a patch having adhesive thereon for application external to a patient's nose, said nasal dilator having means for introducing separating forces in outer nasal wall tissues, thereby expanding the volume of interior nasal passages;
   (b) providing a retainer clip assembly, said retainer clip assembly extending distally of a patient's nose from said nasal dilatator, having means for supporting and retaining medical tubing near the entrance to a patient's nose;
   (c) adhesively applying said nasal dilator to the nose of a patient, said dilator being adapted to introduce separating forces in outer nasal wall tissues, thereby expanding the volume of interior nasal passages; and
   (d) supporting and retaining medical tubing near the entrance to the patient's nose by said retainer clip assembly.

* * * * *